(12) United States Patent
Jabri

(10) Patent No.: US 6,290,495 B1
(45) Date of Patent: Sep. 18, 2001

(54) DENTAL TOOL FOR INSTALLING BRACKETS FOR ORTHODONTIC BRACES

(76) Inventor: S. Jabri, 25 Bluebird La., Naperville, IL (US) 60565

(*) Notice: Subject to any disclaimer, the term of this patent is extended or adjusted under 35 U.S.C. 154(b) by 0 days.

(21) Appl. No.: 09/636,257

(22) Filed: Aug. 10, 2000

(51) Int. Cl.$^7$ ...................................................... A61C 3/00
(52) U.S. Cl. .................................................................. 433/3
(58) Field of Search ................................... 433/3, 24, 72, 433/141

(56) References Cited

U.S. PATENT DOCUMENTS

| | | | |
|---|---|---|---|
| 3,686,762 | * | 8/1972 | Sutter ........................................ 433/3 |
| 4,424,029 | * | 1/1984 | Maijer et al. ............................. 433/3 |
| 4,850,864 | * | 7/1989 | Diamond .................................. 433/3 |

* cited by examiner

Primary Examiner—John J. Wilson
Assistant Examiner—Melba Bumgarner
(74) Attorney, Agent, or Firm—Marshall, O'Toole, Gerstein, Murray & Borun

(57) ABSTRACT

A dental tool for installation of brackets for orthodontic braces is provided which has an adjustable gripping mechanism for gripping the orthodontic bracket and a centering mechanism for centering the bracket on the tooth. The tool is adjustable to fit a wide variety of orthodontic brackets and the tool is further adjustable to enable the bracket to be installed at the proper vertical location on teeth of a wide variety of sizes and lengths.

17 Claims, 1 Drawing Sheet

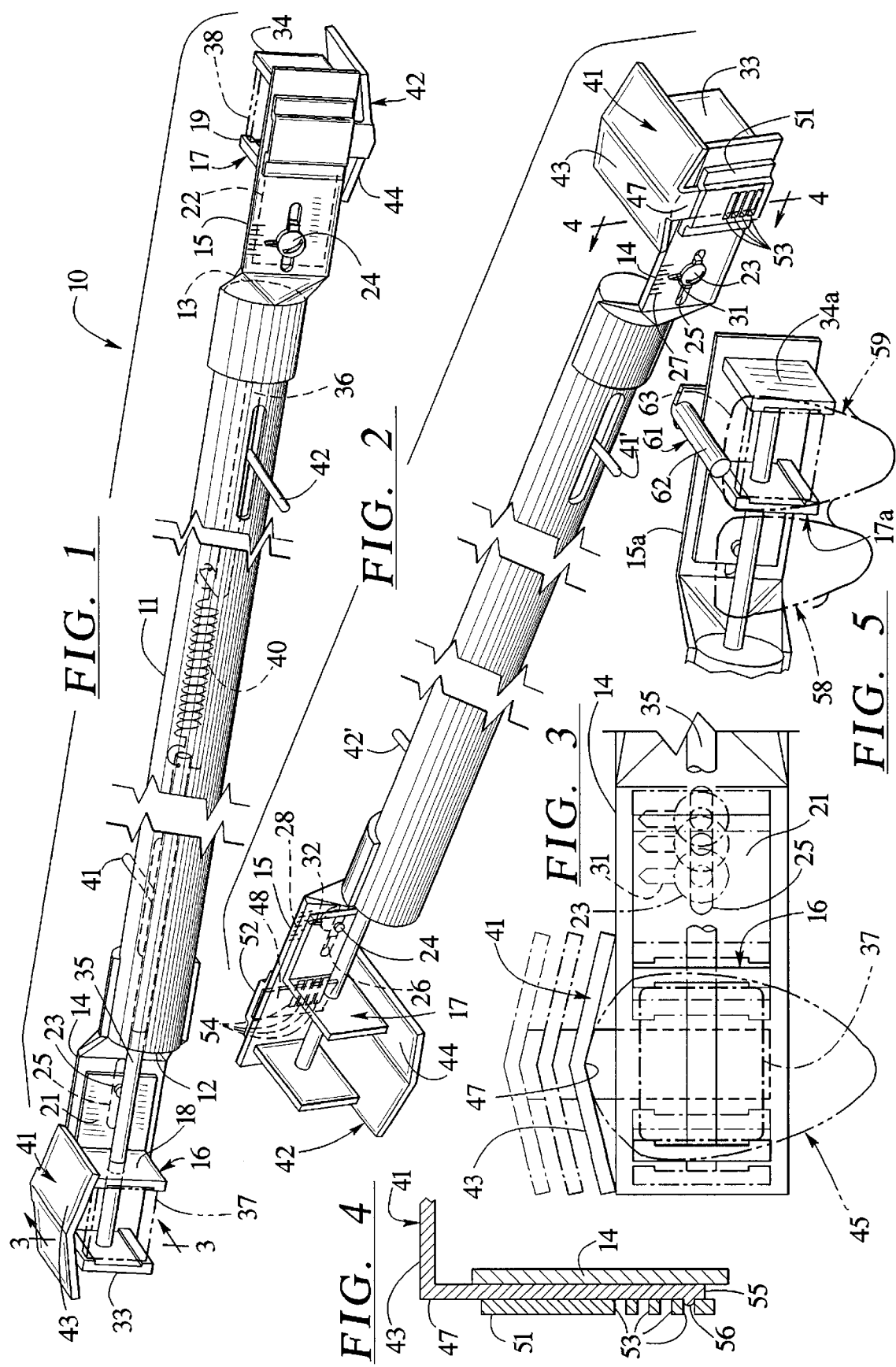

DENTAL TOOL FOR INSTALLING BRACKETS FOR ORTHODONTIC BRACES

FIELD OF THE INVENTION

The present invention relates generally to orthodontic dentistry. More specifically, the present invention relates to a tool used to assist an orthodontist in gluing a bracket for orthodontic braces in a centralized position on a tooth.

BACKGROUND OF THE INVENTION

Modern orthodontic braces include a series of brackets connected by wires. The single bracket is attached to each tooth and then the brackets are connected by wires which are used to apply lateral pressure to the teeth. The brackets are attached to the teeth by glue or cement.

A problem exists in attaching brackets to back teeth or rear molars. Specifically, orthodontists have a difficult time in positioning the brackets on the individual teeth due to the difficult location of the rear molars. Currently, orthodontists simply estimate the appropriate center position for the bracket and glue the brackets to the individual teeth. However, inaccuracies can result when gluing the brackets to the rear molars or, even the front teeth as well. Further, if the brackets are not glued to the teeth in an appropriate laterally centered position, the orthodontic treatment provided by the braces is compromised.

Accordingly, there is a need for an improved method or apparatus for installing orthodontic brackets on teeth in a proper laterally centralized position on the tooth.

SUMMARY OF THE INVENTION

The present invention satisfies the aforenoted need by providing a tool for installing an orthodontic bracket on a tooth in a laterally centralized position on the tooth. The tool of the present invention comprises a handle comprising an end, a generally vertical inner member and a generally vertical outer member. Both the inner and outer members extend generally perpendicularly inward from the end of the handle and are slidably connected to the handle. At least one of the inner and outer members is biased towards the other of the inner and outer members for holding the orthodontic bracket between the inner and outer members. The other of the inner and outer members are adjustable laterally with respect to the handle. A top member is connected to the handle. The top member extends generally perpendicularly inward from the handle and vertically above and beyond the inner and outer members. The top member is for engaging a top of the tooth and centering the inner and outer members with respect to the tooth.

In an embodiment, the top member is vertically adjustable with respect to the inner and outer members.

In an embodiment, the handle further comprises height indicia to indicate the relative height of the top member with respect to the inner and outer members.

In an embodiment, the inner member is adjustable laterally with respect to the handle.

In an embodiment, the handle further comprises indicia to indicate the lateral position of the inner member with respect to a horizontal center of the top member.

In an embodiment, the top member is an arched plate.

In an embodiment, the top member is a plate having inverted V-shape having an obtuse angle.

In an embodiment, the top member comprises a bar.

In an embodiment, the present invention provides a tool for installing an orthodontic bracket on a tooth in a laterally centralized position on the tooth. The tool comprises a handle comprising an end and a support member connected to the end of the handle. A generally vertical inner plate and a generally vertical outer plate extend generally perpendicularly inward from the support member. At least one of the inner and outer plates is biased towards the other of the inner and outer plates for holding the orthodontic bracket between the inner and outer plates. The other of the inner and outer plates is adjustable laterally with respect to the support member. A top plate is connected to the support member. The top plate extends generally perpendicularly inward from the support member and vertically above and beyond the inner and outer plates. The top plate is for engaging a top of the tooth and centering the inner and outer plates with respect to the tooth.

In an embodiment, the present invention provides a tool for installing orthodontic brackets in laterally centralized positions on teeth disposed on opposite sides of a patient's mouth. The tool comprises a handle comprising a first end and a second end and a first support member connected to the first end of the handle. A generally vertical first inner member and a generally vertical first outer member extend generally perpendicularly inward from the first support member and are slidably connected to at least one of the support member or handle. At least one of the first inner and first outer members is biased towards the other of the first inner and first outer members for holding the orthodontic bracket between the first inner and first outer members. The other of the first inner and first outer members is adjustable laterally with respect to the first support member. A first top member is connected to the first support member. The first top member extends generally perpendicularly inward from the first support member and vertically above and beyond the first inner and first outer members. The first top member engages a top of a first tooth and centers the first inner and first outer members with respect to said first tooth. The tool also comprises a second support member connected to the second end of the handle and a generally vertical second inner member and a generally vertical second outer member that extend generally perpendicularly inward from the second support member. At least one of the second inner and second outer members is biased towards the other of the second inner and second outer members. The other of the second inner and second outer members are adjustable laterally with respect to the second support member. A second top member is connected to the second support member, the second top member extends generally perpendicularly inward from the second support member and vertically above and beyond the second inner and second outer members. The second top member engages a top of a second tooth and centers the second inner and second outer members with respect to said second tooth.

In an embodiment, the present invention also provides a method for installing an orthodontic bracket on a tooth. The method comprises the following steps:

grasping the bracket between inner and outer members of a tool comprising a handle comprising an end, both the inner and outer members extending generally perpendicularly inward from the end of the handle and being slidably connected to the handle, at least one of the inner and outer members being biased towards the other of the inner and outer members for holding the bracket between the inner and outer members, the other of the inner and outer members being adjustable laterally with respect to the handle, a top member connected to the handle, the top member extending generally perpendicularly inward from the handle and vertically above and beyond the inner and outer members;

applying glue to at least one of the tooth or the bracket;

engaging a top of the tooth with the top member thereby centering the inner and outer members with respect to the tooth;

sliding the tool inward until the bracket engages the tooth;

holding the bracket against the tooth until the glue sets.

It is therefore an advantage of the present invention to provide an improved tool for installing orthodontic brackets on teeth in a laterally centralized position on the teeth.

Another advantage of the present invention is to provide an improved method for installing orthodontic brackets on teeth in a laterally centralized position.

Other objects and advantages of the present invention will become apparent upon reading the following detailed description and appended claims, and upon reference to the accompanying drawings.

BRIEF DESCRIPTION OF THE DRAWINGS

For a more complete understanding of the present invention, reference should now be made to the embodiments illustrated in greater detail in the accompanying drawings and described below by way of examples of the present invention.

In the drawings:

FIG. 1 is a perspective view of a tool made in accordance with the present invention;

FIG. 2 is a rear perspective view of the tool shown in FIG. 1;

FIG. 3 illustrates the use of the tool shown in FIG. 1 to position a bracket on a tooth;

FIG. 4 is a sectional view taken substantially along line 4—4 of FIG. 1; and

FIG. 5 illustrates an alternative embodiment of a tool made in accordance with the present invention during the installation of a bracket on a tooth.

It should be understood that the drawings are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted. It should be understood, of course, that the invention is not necessarily limited to the particular embodiments illustrated herein.

DETAILED DESCRIPTION OF THE PRESENTLY PREFERRED EMBODIMENTS

FIG. 1 illustrates, in a broken perspective view, a dental tool 10 made in accordance with the present invention. The tool 10 includes a tubular handle 11 with opposing ends 12, 13. The opposing ends 12, 13 are connected to support members 14, 15 respectively. The support member 15 is rotated 180° with respect to the support member 14. The support members 14, 15, which may also be an integral part of the handle 11, are slidably connected to the L-shaped inner members 16, 17 respectively. The support member 15 is rotated 180° with respect to the support member 14 so that a dentist may use the device 10 on all teeth using one hand (i.e. right or left hand). The inner members 16, 17 include the inner plates 18, 19 respectively as well as mounting plates 21, 22 respectively. The mounting plates 21, 22 are connected to the support members 14, 15 respectively by screws 23, 24 respectively. The screws 23, 24 pass through elongated slots 25, 26 in the support members 14, 15 respectively (see FIG. 2). Further, on the backside of the support members 14, 15, indicia 27, 28 are provided which, in combination with the projecting tips 31, 32 which are connected to the screws 23, 24, provide an indication of the lateral positions of the inner members 16, 17 respectively.

Opposite the inner members 16, 17 are the outer members 33, 34. In the embodiment illustrated in FIGS. 1 and 2, the outer members 33, 34 are mounted on rods 35, 36 respectively. The rods 35, 36 pass through the inner members 16, 17 respectively and are biased in a laterally inward direction, or towards the respective inner members 16, 17 by a biasing means such as a spring 40. The inner biasing of the outer members 33, 34 secures the brackets shown in phantom at 37, 38 between the pairs of inner and outer members 16, 33 and 17, 34 respectively. The rods 35, 36 are also equipped with finger grips 41', 42' which enable the orthodontist to separate the pairs of opposing members 16, 33 and 17, 34 so that the brackets 37, 38 can be inserted therebetween.

The tool 10 also includes top members 41, 42. The top members 41, 42, as shown in FIGS. 1–3, include the V-shaped top plates 43, 44 respectively. The obtuse inverted V-shape of the top plates 43, 44 enables the top members 41, 42, and therefore the opposing pairs of side members 16, 33 and 17, 34 to be centered on a tooth 45 as shown in FIG. 3. Specifically, with the correct selection of the bracket 37 and the correct adjustment of the lateral position of the inner member 16, and further with the correct positioning of the apex 47 of the top member 41 on top of the tooth 45, the correct lateral centering of the bracket 37 on the tooth 45 is ensured.

To ensure the correct vertical positioning of the bracket 37 on the tooth 45, the vertical position of the top members 41, 42 is adjustable. Specifically, referring to FIGS. 2 and 4, the top members 41, 42, in addition to the top plates 43, 44 respectively, include downwardly extending rear plates 47, 48 respectively. The rear plates 47, 48 are received in pockets formed by the backside of the support members 14, 15 and the cover plates shown at 51, 52. Each cover plate 51, 52 includes a plurality of slots 53, 54 respectively.

As shown in FIG. 4, the distal end 55 of the rear plate 47 of the top member 41 includes a projecting nub 56 which is received in one of the slots 53. The nub 56 can be received in any one of the plurality of slots 53 to enable vertical adjustment of the top member 41. A similar adjustment is available for the top member 42 as well. The orthodontist will adjust the vertical position of the top members 41, 42 according to the relative size or length of the tooth being treated.

It will be noted that the inverted V-shape for the top members 41, 42 is preferred for the molars and canine teeth having a shape similar or analogous to that of the tooth 45 shown in FIG. 4. However, for the front teeth, which have relatively flat end surfaces such as the teeth 58, 59 as shown in FIG. 5, the inverted V-shape top member is not necessary. Instead, the top members 41, 42 have been replaced by the top member 61 which includes a bar 62 for engaging the top 63 of the tooth 59. The top member 61 may be similarly vertically adjustable like the top members shown at 41, 42.

Accordingly, the tool 10 of the present invention is adjustable so that it can be used for a wide variety of bracket sizes. Brackets come in varying sizes, most of which are listed in the GAC Orthodontics Products Catalog, Copyright 1997 and more recent issues. Information relating to bracket sizes and styles can be attained from GAC International, Inc., 185 Oval Drive, Central Islip, N.Y. 11722-1402.

Further, the tool 10 illustrated in FIGS. 1 and 2 includes bracket holding mechanisms at either ends 12, 13 of the handle 11. Obviously, a tool 10 with only one bracket holding means falls within the spirit and scope of the present invention. Further, tools with top members 41, 42 that are fixed vertically also fall within the spirit and scope of the present invention. In that case, an orthodontist would want to stock a variety of tools 10 with top members 41 or 42 of the varying elevations to accommodate teeth of varying sizes and lengths. The tool 10 may be fabricated from a variety of metallic materials that are easily sterilizable or may be fabricated from plastic materials that are either sterilizable or disposable.

Further, the means for adjusting the spacing between the inner and outer members 16, 33 and/or 17, 34 can be varied. Specifically, the outer members 33, 34 can be laterally adjustable with respect to either the handle 11 or support members 14, 15 and the inner members 16, 17 can be spring biased towards the outer members 33, 34. Further, the configuration of the top members 41, 42 can be varied. An arched configuration, instead of an inverted V-shaped configuration, would be suitable. Instead of the bar configuration for the member 61 shown in FIG. 5, a flat plate or other rectangularly shaped structure would suffice as well. The biasing of the inner and outer members 16, 33 and 17, 34 together need not be accomplished by a spring but could also be accomplished by a clamping or other threaded configuration.

From the above description, it is apparent that the objects and advantages of the present invention have been achieved. While only certain embodiments have been set forth, alternative embodiments and various modifications will be apparent from the above description to those skilled in the art. These and other alternatives are considered equivalents and within the spirit and scope of the present invention.

What is claimed is:

1. A tool for installing an orthodontic bracket on a tooth in a laterally centralized position on the tooth, the tool comprising:
    a handle comprising an end,
    a generally vertical inner member and a generally vertical outer member, both the inner and outer members extending generally perpendicularly inward from the end of the handle and being slidably connected to the handle, at least one of the inner and outer members being biased towards the other of the inner and outer members for holding the orthodontic bracket between the inner and outer members, the other of the inner and outer members being adjustable laterally with respect to the handle,
    a top member connected to the handle, the top member extending inward from the handle, generally perpendicular to the inner and outer members, and vertically above the inner and outer members, the top member for engaging a top of the tooth and centering the inner and outer members with respect to the tooth.

2. The tool of claim 1 wherein the top member is vertically adjustable with respect to the inner and outer members.

3. The tool of claim 2 wherein the handle further comprises height indicia to indicate the relative height of the top member with respect to the inner and outer members.

4. The tool of claim 1 wherein the inner member is adjustable laterally with respect to the handle.

5. The tool of claim 4 wherein the handle further comprises indicia to indicate the lateral position of the inner member with respect to a horizontal center of the top member.

6. The tool of claim 1 wherein the top member is an arched plate.

7. The tool of claim 1 wherein the top member is a plate having an inverted V-shape having an obtuse angle.

8. The tool of claim 1 wherein the top member comprises a bar.

9. A tool for installing an orthodontic bracket on a tooth in a laterally centralized position on the tooth, the tool comprising:
    a handle comprising an end,
    a support member connected to the end of the handle,
    a generally vertical inner plate and a generally vertical outer plate, both the inner and outer plates extending generally perpendicularly inward from the support member, at least one of the inner and outer plates being biased towards the other of the inner and outer plates for holding the orthodontic bracket between the inner and outer plates, the other of the inner and outer plates being adjustable laterally with respect to the support member,
    a top plate connected to the support member, the top plate extending inward from the support member, generally perpendicular to the inner and outer plates, and vertically above the inner and outer plates, the top plate for engaging a top of the tooth and centering the inner and outer plates with respect to the tooth.

10. The tool of claim 9 wherein the top plate is vertically adjustable with respect to the inner and outer plates.

11. The tool of claim 10 wherein the support member further comprises height indicia to indicate the relative height of the top plate with respect to the inner and outer plates.

12. The tool of claim 9 wherein the inner plate is adjustable laterally with respect to the support member.

13. The tool of claim 12 wherein the support member further comprises indicia to indicate the lateral position of the inner plate with respect to a horizontal center of the top plate.

14. The tool of claim 9 wherein the top plate is arched.

15. The tool of claim 9 wherein the top plate has an inverted V-shape having an obtuse angle.

16. A tool for installing orthodontic brackets in a laterally centralized position on teeth disposed on opposite sides of a patient's mouth, the tool comprising:
    a handle comprising a first end and a second end,
    a first support member connected to the first end of the handle,
    a generally vertical first inner member and a generally vertical first outer member, both the first inner and first outer members extending generally perpendicularly inward from the support member being slidably connected to at least one of the support member or handle, at least one of the first inner and outer members being biased towards the other of the first inner and first outer members for holding the orthodontic bracket between the first inner and first outer members, the other of the first inner and first outer members being adjustable laterally with respect to the first support member,
    a first top member connected to the first support member, the first top member extending inward from the first support member, generally perpendicular to the first inner and first outer members, and vertically above the first inner and first outer members, the first top member for engaging a top of a first tooth and centering the first inner and first outer members with respect to the first tooth, a second support member connected to the second end of the handle, a generally vertical second inner member and a generally vertical second outer member, both the second inner and second outer members extending generally perpendicularly inward from the second support member, at least one of the second inner and second outer members for holding the orthodontic bracket between the second inner and second outer members, the other of the second inner and second outer members being adjustable laterally with respect to the second support member, a second top member connected to the second support member, the second top member extending inward from the second support member, generally perpendicular to the second inner and second outer members, and vertically above the second inner and second outer members, the second top member for engaging a top of a second tooth and centering the second inner and second outer members with respect to the second tooth.

17. A method of installing an orthodontic bracket on a tooth, the method comprising the following steps:

grasping the bracket between the inner and outer members of a tool comprising a handle comprising an end, both the inner and outer members extending generally perpendicularly inward from the end of the handle and being slidably connected to the handle, at least one of the inner and outer members being biased towards the other of the inner and outer members for holding the bracket between the inner and outer members, the other of the inner and outer members being adjustable laterally with respect to the handle, a top member connected to the handle, the top member extending inward from the handle, generally perpendicular to the inner and outer members, and vertically above the inner and outer members;

applying glue to at least one of the tooth or the bracket;

engaging a top of the tooth with the top member thereby centering the inner and outer members with respect to the tooth;

sliding the tool inward until the bracket engages the tooth;

holding the bracket against the tooth until the glue sets.

* * * * *